United States Patent [19]  [11] Patent Number: 4,492,651
Sarantakis  [45] Date of Patent: Jan. 8, 1985

[54] CYCLIC HEXAPEPTIDES

[75] Inventor: Dimitrios Sarantakis, West Chester, Pa.

[73] Assignee: American Home Products Corporation, New York, N.Y.

[21] Appl. No.: 554,853

[22] Filed: Nov. 23, 1983

[51] Int. Cl.³ ............................................ C07C 103/52
[52] U.S. Cl. ........................ 260/112.5 S; 260/112.5 R
[58] Field of Search .................. 260/112.5 S, 112.5 R

[56] References Cited

U.S. PATENT DOCUMENTS 4,089,958  5/1978  Freed et al. ........................... 424/250
4,427,661  1/1984  Curley et al. .................. 260/112.5 S

OTHER PUBLICATIONS

Veber et al., *Nature*, 292, 55–58 (1981).
Derwent Abstract 40577 D/23 of EP 29,310.

*Primary Examiner*—Delbert R. Phillips
*Attorney, Agent, or Firm*—Richard K. Jackson

[57] ABSTRACT

Cyclic hexapeptides of the formula:

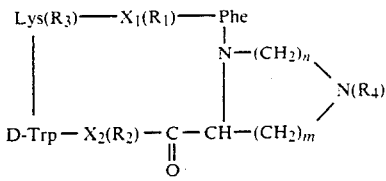

in which
$X_1$ is Thr, Val or Abu;
$X_2$ is Phe, Trp or Tyr;
n is one of the integers 2, 3 or 4;
m is one of the integers 1, 2, 3 or 4;
$R_1$ is hydrogen or a hydroxyl protecting group for Thr;
$R_2$ is hydrogen or a hydroxyl protecting group for Tyr;
$R_3$ is hydrogen or a $N^\epsilon$ protecting group for Lys;
$R_4$ is hydrogen, alkanoyl, aroyl or an amino protecting group;

or pharmaceutically acceptable salts thereof, are inhibitors of growth hormone secretion useful in the treatment of acromegaly and diabetes.

5 Claims, No Drawings

CYCLIC HEXAPEPTIDES

BACKGROUND OF THE INVENTION

Veber et al., Nature 292, 55 (1981) report on potent cyclohexapeptide analogues of somatostatin and their growth hormone inhibiting properties. Among the compounds disclosed is cyclo(Pro-Phe-D-Trp-Lys-Thr-Phe) which contains the cyclic natural amino acid proline in its amino acid sequence.

DESCRIPTION OF THE INVENTION

In accordance with this invention there is provided a group of cyclohexapeptides containing D, L or D,L-1,4-piperazine-2-carboxylic acid in their amino acid sequence as follows:

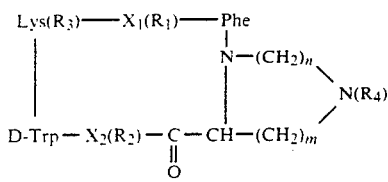

in which
X$_1$ is Thr, Val or Abu;
X$_2$ is Phe, Trp or Tyr;
n is one of the integers 2, 3 or 4;
m is one of the integers 1, 2, 3 or 4;
R$_1$ is hydrogen or a hydroxyl protecting group for Thr;
R$_2$ is hydrogen or a hydroxyl protecting group for Tyr;
R$_3$ is hydrogen or a N$^\epsilon$ protecting group for Lys;
R$_4$ is hydrogen, alkanoyl of 2 to 6 carbon atoms, aroyl of 7 to 10 carbon atoms or an amino protecting group, or a pharmaceutically acceptable salt thereof. These cyclic hexapeptides, as end products devoid of protecting groups, inhibit the release of growth hormone and as such, they are useful in the treatment of disease conditions characterized by excessive blood levels of growth hormone such as acromegaly and diabetes. The pharmaceutically acceptable salts of the compounds of this invention are those non-toxic addition salts produced by known methods from acids conventionally employed with pharmaceuticals such as hydrochloric, hydrobromic, sulfuric, phosphoric, polyphosphoric, maleic, acetic, citric, benzoic, succinic, malonic or ascorbic acid, and the like.

The cyclic and linear intermediate polypeptides employed in the production of the end compounds of this invention represent an additional compound aspect of the invention. The intermediates comprise the protected cyclic hexapeptides embraced by the structural formula presented supra and the linear amino acid sequences on or off the hydroxymethylated polystyrene resin support employed in their solid phase manufacture, as represented by the following formula:

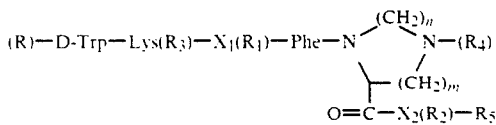

in which
X$_1$ is Thr, Val or Abu;
X$_2$ is Phe, Trp or Tyr;
n is one of the integers 2, 3 or 4;
m is one of the integers 1, 2, 3 or 4;
R is hydrogen or an α-amino protecting group;
R$_1$ is a hydroxyl protecting group for Thr;
R$_2$ is a hydroxyl protecting group for Tyr;
R$_3$ is an N$^\epsilon$ protecting group for Lys;
R$_4$ is alkanoyl of 2 to 6 carbon atoms, aroyl of 7 to 10 carbon atoms or an amino protecting group; and
R$_5$ is —NHNH$_2$ or the residue of an oxypolystyrene resin.

The protecting groups employed during preparation of the linear intermediates are conventional in solid phase polypeptide synthesis. Thus, in the above formula, the protecting group embraced in the definition of R may be formyl, trifluoroacetyl, phthalyl, p-chlorobenzyloxycarbonyl, p-nitrobenzyloxycarbonyl, tert-butyloxycarbonyl (Boc), 2,2,2-trichloroethoxycarbonyl, amyloxycarbonyl, cyclopentyloxycarbonyl, cyclohexyloxycarbonyl, trityl, etc., the preferred group being tert-butyloxycarbonyl.

The hydroxyl protecting groups R$_1$ and R$_2$ for tyrosyl or threonyl are benzyl, p-methoxybenzyl, p-chlorobenzyl, p-nitrobenzyl, trityl, benzyloxycarbonyl, p-methoxybenzyloxycarbonyl, and the like. The benzyl group is preferred for protecting the tyrosyl and threonyl moiety.

Protecting groups for the nitrogen (ε) atom of lysine (R$_3$) and the nitrogen atom of the piperazine ring include tosyl, benzyloxycarbonyl (Z), 2-chlorobenzyloxycarbonyl, and tert-butyloxycarbonyl, preferably the 2-chlorobenzyloxycarbonyl group. The benzyloxycarbonyl group is preferred for the piperazine nitrogen atom.

The support employed in the solid phase synthesis of these compounds is a chloromethylated or hydroxymethylated polystyrene resin cross-linked with divinylbenzene. These resins are prepared by known methods and are commercially available in the art.

The following examples illustrate the preparation of

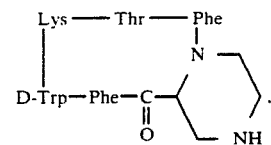

which is representative, in its solid phase preparation and biological activity, of the other compounds of the invention.

EXAMPLE 1

4-Benzyloxycarbonyl-2-tert-butyloxycarbonyl-piperazine carboxylic acid

DL-4-CBZ-2-piperazine carboxylic acid, which is described in U.S. Pat. No. 4,089,958 (10 g) was dissolved in 40 ml water and 10 ml tert-butanol, mixed with 1.33 g of NaOH and then di-tert-butyl-dicarbonate (8.07 g) was added dropwise over a period of one hour. An additional quantity of tert-butanol (40 ml) was added followed by 40 ml water and the mixture was stirred at room temperature overnight. Water was added (300 ml) and the mixture was extracted with pentane 3 times. The aqueous layer was cooled in an ice-bath and acidified to pH 2-3 with KHSO₄. The milky mixture was extracted with ethylacetate. The organic solution was dried over MgSO₄ and evaporated to afford a solid (4 g).

TLC Silica gel precoated glass plates—$R_f$(CHCl₃—MeOH, 4:1, v/v) 0.61.

Analysis for: $C_{18}H_{24}N_2O_6$, Calculated: C, 59.33; H, 6.64; N, 7.69, Found: C, 59.51; H, 6.80; N, 7.49.

Mass Spectral Analysis: (M⁺ +1) 365.

EXAMPLE 2 tert-Butyloxycarbonyl-D-tryptophyl-N-2-chlorobenzyloxycarbonyl-L-lysyl-O-benzyl-L-threonyl-L-phenylalanyl-DL-4-benzyloxycarbonyl-2-piperazinocarboxyl-L-phenylalanine hydroxymethyl polystyrene ester Polymeric ester, BOC-Phe-O-Resin containing 1.15 mmoles/g phenylalanine (15 g) was treated according to schedule A shown below, for the incorporation of DL-4-benzyloxycarbonyl-2-tert-butyloxycarbonylpiperazine carboxylic acid (PCA), BOC-Phe-OH, BOC-Thr(BZL)OH, BOC-Lys(ClCBZ)OH and finally BOC-D-Trp-OH to afford the title peptidoresin. Aminoacid analysis: Phe(2) 2, Thr(1) 0.64, Trp (destroyed), Lys+-PCA co-elute.

Schedule A: (for treatment of the resin ester)
1. Wash with methylene chloride (CH₂Cl₂), three times.
2. Treat with trifluoroacetic acid-methylene chloride (1:1, v/v) containing 5% 1,2-ethane dithiol for 5 minutes.
3. Repeat Step 2 for 25 minutes.
4. Wash with CH₂Cl₂, three times.
5. Wash with dimethylformamide (DMF).
6. Treat with 12% triethylamine in DMF for 3 minutes.
7. Wash with DMF.
8. Wash with CH₂Cl₂, three times.
9. Treat with 4 equivalents of the appropriate protected amino acid in CH₂Cl₂—DMF and stir for 5 minutes.
10. Add in two portions over a 30 minute period; 5 equivalents of diisopropylcarbodiimide dissolved in CH₂Cl₂. Allow reaction to proceed for 6 hours.
11. Wash with DMF, three times.
12. Wash with CH₂Cl₂, three times.
13. Test by ninhydrin reaction according to the procedure of Kaiser et. al., Annal. Biochem., 34, 595 (1970). In case of incomplete reaction, repeat Steps 9 to 13, as above.

EXAMPLE 3

D-Tryptophyl-N^ε-2-chlorobenzyloxycarbonyl-L-lysyl-O-benzyl-L-threonyl-L-phenylalanyl-4-benzyloxycarbonyl-2-piperazinocarboxyl-L-phenylalanyl-hydrazide The peptido resin of the previous example was treated with trifluoroacetic acid as follows in order to remove the N-tert-butyloxycarbonyl group:
1. Wash with methylene chloride (CH₂Cl₂), three times.
2. Treat with trifluoroacetic acid-methylene chloride (1:1, v/v) containing 5% 1,2-ethane dithiol for 5 minutes.
3. Repeat Step 2 for 25 minutes.
4. Wash with CH₂Cl₂, three times.
5. Wash with dimethylformamide (DMF).
6. Treat with 12% triethylamine in DMF for 3 minutes.
7. Wash with DMF.
8. Wash with CH₂Cl₂, three times.

The partially deprotected peptido resin (25.5 g) was suspended in dimethylacetamide (DMA) (225 ml) and treated with 25 ml of anhydrous hydrazine. The suspension was stirred for 3 hours, filtered, and the filtrate was evaporated to a small volume. The residue was triturated with 600 ml brine to afford a gummy material which was washed by decantation and dried under vacuo over P₂O₅, yield 15.95. TLC indicated the presence of a mixture of a major component accompanied by 3 minor ones.

EXAMPLE 4

Cyclo-(D-Tryptophyl-N^ε-2-chlorobenzyloxycarbonyl-L-lysyl-O-benzyl-L-threonyl-L-phenylalanyl-4-benzyloxycarbonyl-DL-2-piperazinocarboxyl-L-phenylalanyl The partially protected hexapeptide hydrazide (15.95 g) of Example 3 was dissolved in 200 ml DMF, cooled at −10° C., and mixed with 17.7 ml of 2.9N HCl in ethyl acetate. The solution was cooled further at −25° C. and then isoamylnitrite (50% solution) (10.3 ml) was added. The reaction mixture was allowed to stir for 20 minutes after which time it was poured into 4 liters of DMF and the pH was adjusted to 9 with triethylamine. The dilute reaction mixture was kept in the cold room, temperature ca. 5° C., for 3 days and then evaporated to dryness. The residue was dissolved in a mixture of DMF/water, 3:1, v/v and passed through a mixed-bed ion exchange resin AG 501-X8, twice. The solution was evaporated to dryness. The residue was treated with 500 ml water to afford a solid which was dried over P₂O₅, yield 12.96 g.

EXAMPLE 5

Cyclo-(D-Tryptophyl-L-lysyl-L-threonyl-L-phenylalanyl-DL-2-piperazinocarboxyl-L-phenylalanyl)

Part of the material of the previous example (7.96 g) was mixed with 20 ml anisole and treated with 200 ml liquid HF for one hour in an ice-bath and under exclusion of air. The excess liquid HF was removed under vacuo as fast as possible (ca. one hour) and the residue was taken in 40 ml of 50% acetic acid and diluted to 500 ml with water. The aqueous solution was extracted with ethyl acetate twice and the aqueous phase was lyophilized twice to yield the title compound as a solid diacetate salt, 5.95 g.

TLC, silica gel F-254 precoated glass plates, elution with CHCl₃—CH₃OH—NH₄OH, 70:30:5, v/v shows one main spot $R_f$ 0.70 and traces of impurities. Aminoacid analysis: Thr(1) 1.06, Trp(1) 0.85, Phe(2) 2.

This crude material was chromatographed through a column of silica gel 60 (2.5×40 cm) which was eluted with CHCl₃—CH₃OH—NH₄OH, 70:30:5, v/v. The progress of the elution was followed by TLC. Fractions which contained only the desired compound were combined and evaporated to dryness. The residue was taken in some n-butanol-water and lyophilized to yield 1.55 g of pure material.

TLC: Silica gel 254-F precoated glass plates $R_f$(CHCl₃—CH₃OH—NH₄OH, 70:30:5, v/v) 0.70

Aminoacid analysis: Thr(1) 1.02, Phe(2) 2, Trp(1) 1, Lys and

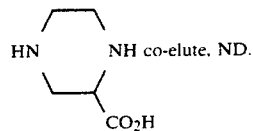

HPLC: μBondapak $C_{18}$ column, 66% 1M $NH_4OAc$, pH 4, 34% $CH_3CN$, 254 nm, two peaks K=1.2, 33% K=1.6, 64.8% (isomers) and 2.2% impurities.

The potent inhibition of growth hormone secretion was established for the compounds of this invention by subjecting the representative product of Example 5 to the following standard procedure involving suppression of growth hormone release in arginine stimulated rats:

Albino male rats are administered Nembutal intraperitoneally at a dose of 50 milligrams per kilogram. Fifteen minutes later a subcutaneous injection of the product of Example 5 is administered. Ten minutes later 0.5 milliliters of arginine (300 milligrams per milliliter, pH 7.2) is injected into the heart. Five minutes after receipt of the arginine the rats are decapitated and blood is collected into Trasylol-EDTA. An appropriate aliquot is assayed for growth hormone (GH) by radioimmuno-assay. The results of the test procedure were compared with those obtained in the same manner with Compound 8 of Table 2 disclosed by Veber et al., loc. cit., as follows:

| Dose of Peptide μg/kg | Plasma GH Levels (ng/ml) | |
|---|---|---|
| | Veber et al. Compound 8 | Example 5 |
| 10.0 | 126 ± 6 | 95 ± 5 |
| 1.0 | 169 ± 19 | 113 ± 9 |
| 0.1 | 278 ± 89 | 175 ± 20 |

From these data it can be seen that the compound of this invention is approximately ten times as potent as the product of the Veber et al. reference in that the suppression of GH at a 0.1 μg/kg dose of the product of Example 5 is about the same as that obtained with the Veber et al. compound at 1.0 μg/kg. The same analysis applies to the 1.0 μg/kg and 10.0 μg/kg doses.

As with administration of any therapeutic agent used in the treatment of diabetes mellitus, the compounds of this invention must be individualized for the patient under guidance and close control for the attending physician to reach optimum blood level of growth hormone. Doses for achieving the desired state vary with the condition of the patient, such as age, amount of endogenous insulin produced, the presence of glucagon secreting tumors, the route of administration, the duration of treatment, severity of the condition being treated, etc.

Thus, the compounds of this invention may be administered alone or in combination with insulin with or without carriers or excipients conventional to the route of administration selected, which may be oral, intravenous, subcutaneous, intramuscular, intranasal, intrarectally, etc. Suitable pharmaceutical compositions for application are apparent to those skilled in the art.

What is claimed is:

1. A compound of the formula:

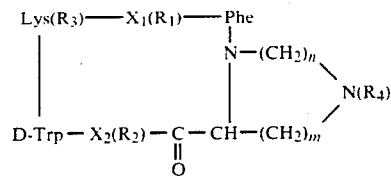

in which
  $X_1$ is Thr, Val or Abu;
  $X_2$ is Phe, Trp or Tyr;
  n is one of the integers 2, 3 or 4;
  m is one of the integers 1, 2, 3 or 4;
  $R_1$ is hydrogen or a hydroxyl protecting group for Thr;
  $R_2$ is hydrogen or a hydroxyl protecting group for Tyr;
  $R_3$ is hydrogen or a $N^\epsilon$ protecting group for Lys;
  $R_4$ is hydrogen, alkanoyl of 2 to 6 carbon atoms, aroyl of 7 to 10 carbon atoms or an amino protecting group,
or a pharmaceutically acceptable salt thereof.

2. The compound of claim 1 which is cyclo(D-tryptophyl-L-lysyl-L-threonyl-L-phenylalanyl-D.L-2-piperazinocarboxyl-L-phenylalanyl).

3. A compound of the formula

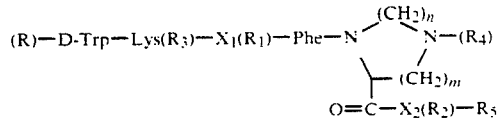

in which
  $X_1$ is Thr, Val or Abu;
  $X_2$ is Phe, Trp or Tyr;
  n is one of the integers 2, 3 or 4;
  m is one of the integers 1, 2, 3 or 4;
  R is hydrogen or an α-amino protecting group;
  $R_1$ is a hydroxyl protecting group for Thr;
  $R_2$ is a hydroxyl protecting group for Tyr;
  $R_3$ is an $N^\epsilon$ protecting group for Lys;
  $R_4$ is alkanoyl of 2 to 6 carbon atoms, aroyl of 7 to 10 carbon atoms or an amino protecting group; and
  $R_5$ is $-NHNH_2$ or the residue of an oxypolystyrene resin.

4. The compound of claim 3 which is tert-butyloxycarbonyl-D-tryptophyl-N-2-chlorobenzyloxycarbonyl-L-lysyl-O-benzyl-L-threonyl-L-phenylalanyl-DL-4-benzyloxycarbonyl-2-piperazinocarboxyl-L-phenylalanine hydroxymethyl polystyrene ester.

5. The compound of claim 3 which is D-tryptophyl-N 2-chlorobenzyloxycarbonyl-L-lysyl-O-benzyl-L-threonyl-L-phenylalanyl-4-benzyloxy-carbonyl-2-piperazinocarboxyl-L-phenylalanyl hydrazide.

* * * * *